United States Patent
Jiang et al.

(10) Patent No.: US 8,246,933 B2
(45) Date of Patent: Aug. 21, 2012

(54) AEROSOL METHOD FOR NANO SILVER-SILICA COMPOSITE ANTI-MICROBIAL AGENT

(75) Inventors: Xingmao Jiang, Albuquerque, NM (US); C. Jeffrey Brinker, Albuquerque, NM (US); Yong Lin, Albuquerque, NM (US); Yung-Sung Cheng, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 349 days.

(21) Appl. No.: 12/324,318

(22) Filed: Nov. 26, 2008

(65) Prior Publication Data
US 2009/0175948 A1    Jul. 9, 2009

Related U.S. Application Data

(60) Provisional application No. 60/991,380, filed on Nov. 30, 2007.

(51) Int. Cl.
*A61K 9/14* (2006.01)
*A01N 59/16* (2006.01)

(52) U.S. Cl. .......... 424/46; 424/489; 424/618; 977/810; 977/906; 977/915

(58) Field of Classification Search .................. 424/46, 424/489, 618; 977/810, 906, 915
See application file for complete search history.

(56) References Cited

U.S. PATENT DOCUMENTS

| 7,384,680 B2 * | 6/2008 | Bi et al. ................... 428/143 |
| 7,795,007 B2 * | 9/2010 | Abbott et al. ............. 435/287.2 |
| 2005/0149169 A1 * | 7/2005 | Wang et al. .............. 623/1.15 |

OTHER PUBLICATIONS

Weiping et al, Synthesis and structural and optical properties of mesoporous silica containing silver nanoparticles, J. PHYs. Condens. Matter 9 (1997) 7257-7267.*
Gvidona et al, On the nature of the processes occuring in silver doped SiO2 films under heat treatment, J. Sol-Gel Sci Technol (2008) 45:143-149.*

* cited by examiner

*Primary Examiner* — Mina Haghighatian
(74) *Attorney, Agent, or Firm* — MH2 Technology Law Group, LLP

(57) ABSTRACT

A method of forming and resulting nano-structured composite includes atomizing a mixture of an amount of each of aminopropyltriethoxysilane, $AgNO_3$, DI water, and ethanol in a carrier gas; heating the atomized droplets at a selected temperature for a time sufficient to reduce the Ag to its elemental form in a silica matrix; and outputting the nano structured composite particles. A predetermined heating time is from about 0.01 to about 40 seconds and a selected heating temperature is from about 200 to about 800° C. The nano structured composite includes a plurality of nano particles at a contact surface of the composite, dispersed throughout and at a contact surface of the composite, or dispersed throughout the composite.

14 Claims, 3 Drawing Sheets

AEROSOL METHOD FOR NANO SILVER-SILICA COMPOSITE ANTI-MICROBIAL AGENT

RELATED APPLICATIONS

This application claims priority from U.S. Provisional Patent Application Ser. No. 60/991,380, filed Nov. 30, 2007, which is hereby incorporated by reference in its entirety.

GOVERNMENT RIGHTS

The present invention was made with Government support under Grant No. EE C0210835 awarded by the National Science Foundation, National Institute for Respiration Therapy; Subaward No. SC GG10306113743 awarded by MURI/University of Virginia under the USAF/AFOSR Prime Grant No. F49620-01-1-0352; and USAF/AFOSR Grant No. FA9550-04-1-0087 The Government has certain rights to the invention.

FIELD OF THE INVENTION

The present invention relates generally to aerosols and, more particularly, to a method for forming an aerosol of nano silver-silica composite for use as an anti-microbial agent.

BACKGROUND OF THE INVENTION

Certain metals have been known to include anti-microbial properties. These anti-microbial properties are ideal for use in materials having a sustained efficacy against bacteria. Exemplary metals having anti-microbial properties include, for example, silver, copper, zinc, gold, platinum, and palladium.

In the past, silver has been used in the food service industry and for home use, for example in goblets and silverware, because it is believed to inhibit diseases. In particular, colloidal silver is thought to be useful as a strong, natural antibiotic, and for prevention of infections. Without being limited to theory, it is believed that the high particle surface area of colloidal silver enables high bioavailability for maximum effectiveness. Colloidal silver has been found effective against germs, bacteria, infections, parasites, viruses, fungus and pathogens. In addition, colloidal silver has an infinite shelf life. When colloidal silver is in proximity to a virus, fungus, bacterium, or any other single-celled pathogen, it acts as a catalyst to disable the oxygen metabolism enzyme without incurring harm to human enzymes or the human body's chemistry. Thus colloidal silver is safe for humans, animals, plants, and all multi-celled living mater.

Silver has been successfully used in treating more than 650 diseases. A non-limiting list of treated conditions includes acne, AIDS, allergies, appendicitis, arthritis, athlete's foot, tuberculosis, bladder inflammation, blood parasites, blood poisoning, boils, bubonic plague, burns, cancer, candida, chilblains, cholera, colitis, conjunctivitis, cystitis, diabetes, dysentery, eczema, fibrositis, gastritis, gonorrhea, hay fever, herpes, impetigo, indigestion, keratitis, leprosy, leukemia, lupus, lymphangitis, lyme disease, malaria, meningitis, neurasthenia, parasitic infections both viral and fungal, pneumonia, pleurisy, prostate, psoriasis, purulent ophthalmia, rhinitis, rheumatism, ringworm, scarlet fever, septic conditions of the eyes, ears, mouth and throat, seborrhea, septicemia, shingles, skin cancer, staph infections, strep infections, syphilis, thyroid, tonsillitis, toxemia, trachoma, trenchfoot, dermatitis, all forms of virus, wars, whooping cough, yeast infection, stomach ulcer, and also canine parvovirus and other veterinary uses.

In addition, colloidal silver is effective for severe acute respiratory syndrome (SARS) which is caused by SARS coronavirus. Also, certain disinfectants are known and include ethanol, sodium hypochlorite, iodophor, peracetic acid, formaldehyde, glutaraldehyde and ethylene oxide gas. However, these disinfectants are only temporary and only effective with a direct application to the disinfecting site. Thus, these disinfectants are not suitable for sustained effectiveness.

A major challenge facing the pharmaceutical industry is how to cope with increasing drug resistance of pathogens to commercially available drugs in view of mutation of chromosomal genes. By way of example, each year, nearly 9 million people develop tuberculosis, of which about two million will die. The emergence and spread of multidrug-resistant (MDR) Mycobacterium Tuberculosis (MT) represents a worldwide healthcare problem because of the difficulty in treating these infections.

It has been demonstrated that colloidal silver does not interact or interfere with other medicines being taken by a patient. More specifically, colloidal silver does not form toxic compounds or react with anything other than a germ's oxygen-metabolizing enzyme. Thus, it follows that no tolerance to colloidal silver will develop through mutation. The high particle surface area can enable high bioavailability for maximum effectiveness. It is the discovery of the inventors that high particle surface area can be obtained in a nanosilver product.

Currently, almost all nanosilver products are found in water or organic solvent such as dimethylformamide (DMF), dimethylacetamide (DMAC), ethylene glycol (EG), and glycerine as colloids. Silver colloid particles having narrow size distribution are manufactured by electrolysis, reducing agents such as hydrazine, $NaBH_4$, $LiAlBH_4$, or by radiation exposure. The manufactured silver corpuscles are collected by a centrifugal separator, and then dispersed again in the original medium. A particle of nano size always forms an oxidized film on a surface thereof when it is exposed to air. An antioxidant such as butylhydroxy toluene and vitamin E derivative are used to prevent oxidation of a surface formed of metal particles. The nano size particles tend to agglomerate due to a tendency of each particle to minimize its surface area. Accordingly, it is difficult to obtain separated nano particles. In an effort to maintain separate particles, surface active agents can be used. Examples of these surface active agents can include sodium dodecyl sulfate, polyvinyl alcohol, and polyvinylpyrollidone. The additives block growth of the composite metal particles, and thereby keep the particle at a nano size.

In order to maintain a resistance to high temperatures, silver based inorganic anti-microbial agents can comprise silver carried on an inorganic compound. A carrier which stably holds the silver nanoparticles can include active charcoal (JP Patent Publication No. 49-61950), soluble glass (JP Patent Publication No. 63-181002), zirconium phosphate (JP Patent Publication No. 3-83905), apatite, silica, titanium oxide, porous ceramics, and titanium. As an antibacterial agent, nanosilver can be distributed in the vicinity of the surface of a resin material. The resultant composition can exhibit antibacterial properties, mildew resistance, permanence of mildew resistance and weatherability such as heat resistance and ultraviolet light resistance.

Another method for combining silver and silica can be found in DE 96 50 500A1 in which a one-step pyrogenic silica doping is modified and a process is disclosed for preparation of pyrogenic silica doped with silver or silver oxide. The doping process differs from a previous "co-fumed" process in which gaseous starting materials (for example $SiCl_4$ vapor and $AlCl_3$ vapor) are premixed and burnt together in a flame reactor. The silver salt/water aerosol produced in the aerosol generator is passed through a heating zone with a light carrier gas stream. The aerosol is mixed homogeneously with $SiCl_4$ vapor and $H_2$, and $O_2$ mixture used for the flame oxidation or the flame hydrolysis before the reaction. Then, the aerosol/gas mixture is reacted in the flame and the resulting pyrogenically prepared silicas doped with silver or silver oxide are separated from the gas stream.

As a source for silver growth, however, flame oxidation and flame hydrolysis are far different at a high temperature. The multiple-phase, multi-reaction, high temperature process is too complicated for scale-up and a large financial investment is needed. Further, the nano size of the silver particles is difficult if not impossible to maintain due to their quick reduction, nucleation, agglomeration and the difficulty in controlling Ag crystalline growth at high temperatures. Because of these and other difficulties, the silver distribution is non-uniform, resulting in reduced drug efficiency and reduced bioavailability. Similarly, embedded silver in fumed silica is less available because the fumed silica is less soluble. In addition, there is a severe corrosion problem and HCl residue still adhering to the silica will need to be removed at elevated temperatures, resulting in further growth of silver crystallites.

It would be desirable, therefore, and a need exists in the art, to utilize the benefits of colloidal silver in a form that presents a high particle surface area, which is reproducible, convenient for transportation, storage, and dispensation with required dosage, thermally stable, having an elongated disinfection time, and a long shelf life.

BRIEF DESCRIPTION OF THE DRAWINGS

The accompanying drawings, which are incorporated in and constitute a part of this specification, illustrate embodiments of the invention and together with the description, serve to explain the principles of the invention. In the figures.

DESCRIPTION OF THE EMBODIMENTS

Reference will now be made in detail to exemplary embodiments of the invention, examples of which are illustrated below and in the accompanying drawings. Wherever possible, the same reference numbers will be used throughout the drawings to refer to the same or like parts.

Figure 1:
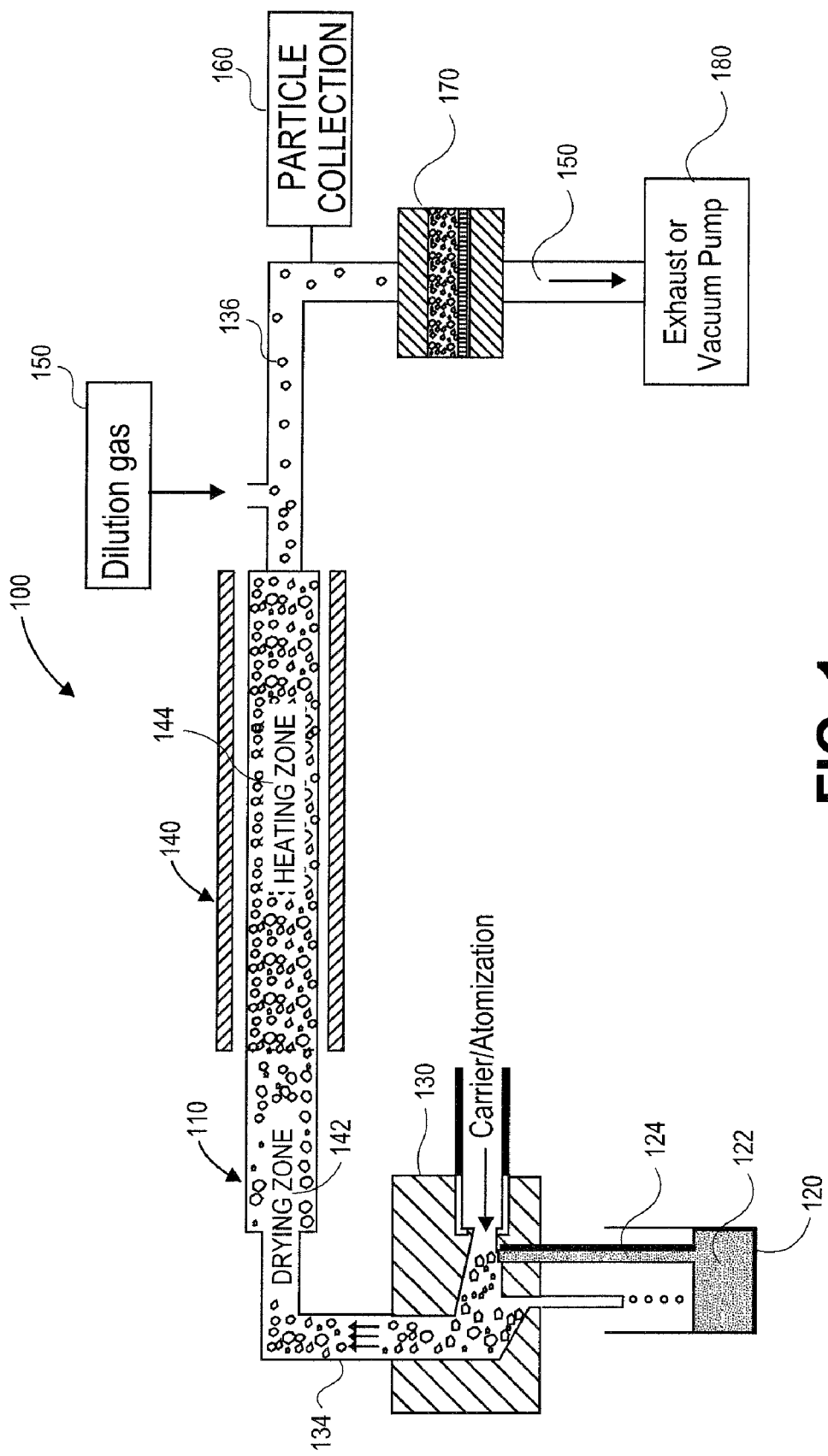
FIG. 1 is a side view of an apparatus for aerosol assisted evaporation induced self-assembly of nano composite particles according to exemplary embodiments herein.

Referring first to FIG. 1, an apparatus 100 for aerosol assisted evaporation induced self-assembly (EISA) of nano composite particles is depicted. It should be readily apparent to those of ordinary skill in the art that the apparatus depicted in FIG. 1 represents a generalized schematic illustration and that other components may be added or existing components may be removed or modified. Moreover, the apparatus 100 may be implemented using software components, hardware components, or combinations thereof.

The aerosol assisted ESIA 100 can include an aerosol reactor 110, a supply reservoir 120, an atomizer 130, a furnace 140, a dilution gas source 150, a particle collector 160, a filter 170, and an exhaust or vacuum pump 180. The aerosol reactor 110 functions as a contained chamber in which various reactions can occur, and along which the components of supply reservoir 120, atomizer 130, furnace 140, dilution gas source 150, particle collector 160, and exhaust 170 are positioned. These components can be operatively connected in series, typically in the order provided above, however one skilled in the art can alter components according to processing parameters.

The aerosol reactor 110 can further be of any suitable length, diameter or dimension, and material to complete the necessary reactions. For example, the aerosol reactor 110 can be formed of a glass and in a tubular shape with varying dimensions as needed at stages of the reactor.

The supply reservoir 120 can include a precursor 122 therein. The precursor 122 can be in the form of a solution. A feed tube 124 can connect the supply reservoir 120 to the atomizer 130 in order to supply the precursor solution 122 via pump, capillary, suction, or the like to the atomizer 130.

In accordance with various embodiments, an exemplary precursor 122 can include about 5 g of aminopropyltriethoxysilane along with about 0.5 g to about 2 g of $AgNO_3$. Further, about 25 g deionized (DI) water and about 12 g of ethanol can be provided in the precursor, for inclusion in the atomized mixture. In addition, silver can be present in an amount of about 1 to about 80 wt % of the final nano-composites. A molar ratio of aminosilane to silver can be about 0.1:1 to about 10:1, the molar ratio selectively adjusted to control silver distribution and size.

The atomizer 130, in addition to being supplied with the precursor solution 122, can include a carrier/atomization gas supply 132. The atomizer 130 initiates a reaction of the precursor solution 122 and the carrier/atomization gas supply 132 to generate aerosol droplets/atomizing gas mixture 134.

According to exemplary embodiments, the atomizer 130 can be a TSI 9302A atomizer, using one or more of nitrogen and air as the carrier gas supply 132.

The furnace 140 can process the atomized mixture 134. According to various embodiments, processing can be at a predetermined temperature and for a predetermined time. Even further, the furnace 140 can be configured to include a drying zone 142 and a heating zone 144. The drying zone 142 can be positioned at an intake of the furnace 140, and downstream of the atomizer 130. The heating zone 144 can be downstream (subsequent to) the drying zone 142. In the drying zone, solvents evaporate at room temperature or low temperature. So the droplets are enriched for nonvolatile species before entering heating zone kept at a higher temperature for further self-assembly. Each of the drying zone 142 and heating zone 144 can be of a length to enable suitable drying and heating of the atomized mixture 134 over the time required.

According to various embodiments, a residence heating time within the furnace 140 can be from about 0.01 to about 40 seconds at a temperature from about 200 to about 800° C. Further, the furnace 140 can be maintained at a temperature of about 400° C. over a length thereof. The furnace 140 can include a Lindberg furnace as known in the art.

The apparatus 100 can further include the dilution gas supply 150, positioned upstream or downstream of the furnace 140. The dilution gas supply 150 can be provided to introduce dilution gas 152 into and thereby dilute the atomized mixture 134, adjust residence time of aerosol droplets in the reaction reactor, and control aggregation of aerosol particles. The dilution gas supply can be nitrogen, for example. The atomized mixture 134 is thus dispersed to distinguish the suspended nano-composite particles 136 therein.

At the particle collector 160, the temperature is set above certain temperature, for example, 80° C. to keep aerosol particles dry and prevent their agglomeration. The nano-composite particles 136 of a core-shell configuration can be carried by carrier gas and collected on filter 170.

The filter 170 can be provided subsequent to the particle collection section 160. At the filter 170, collected particles 136 can be extracted from the dilution gas 152. According to exemplary embodiments, the powder can be collected on PTFE filter paper 170. The particles can therefore be collected by vacuum 180 or by dilution and atomizing gas air flow with a pressure drop.

The exhaust or vacuum pump 180 can also be provided to expel dilution gas 152 subsequent to extracting particles 136 at the filter 170.

The above described apparatus can be used in exemplary methods for extracting (collecting) nanostructured particles with aerosol assisted evaporation induced self-assembly as given by way of example herein.

Figure 2:
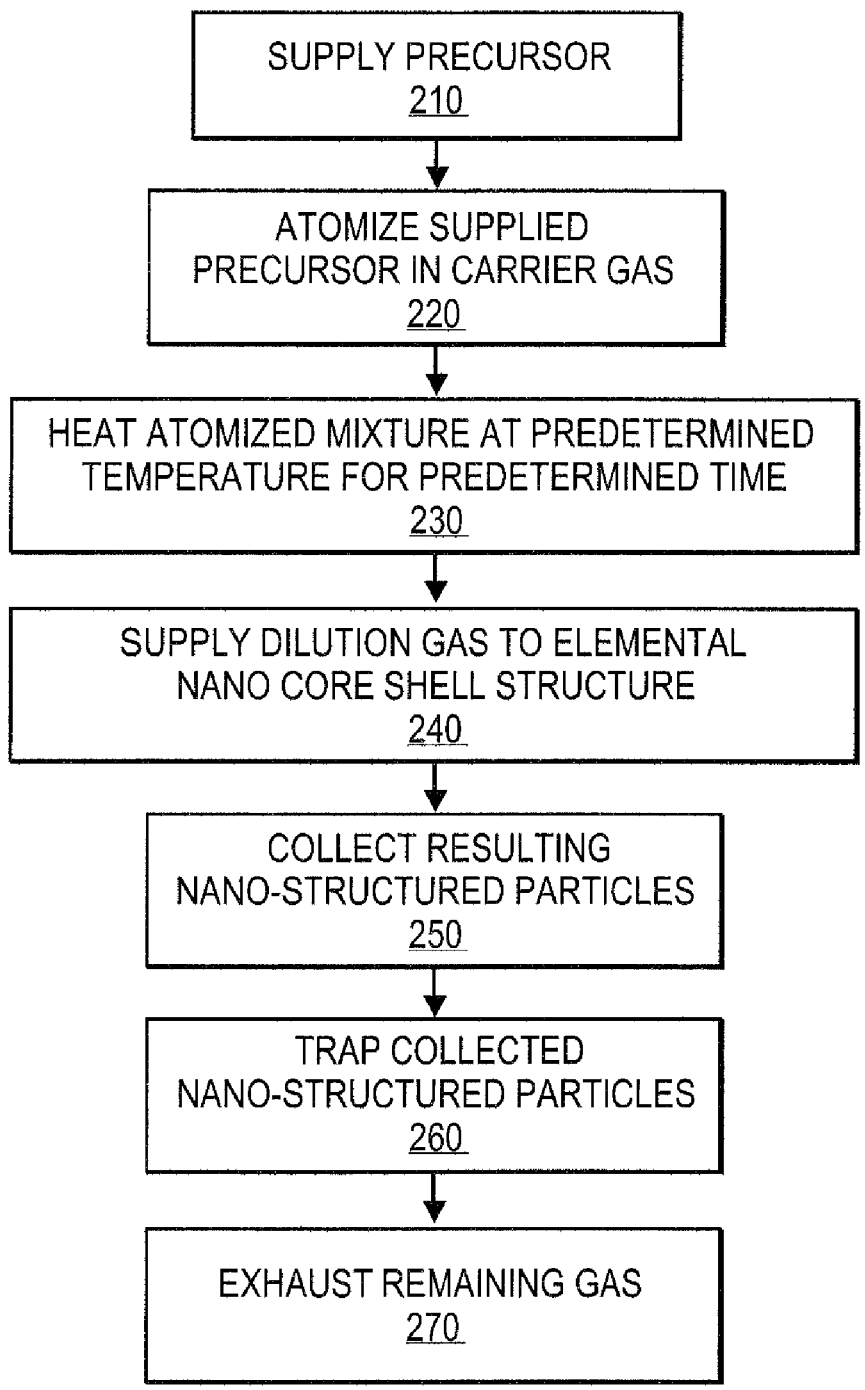
FIG. 2 depicts a method of forming the nano composite particles according to exemplary embodiments herein.

According to various embodiments, an exemplary method 200 of collected nano silver-silica particles is depicted in FIG. 2. One of ordinary skill in the art will understand that the example provided is exemplary and that other steps can be added or existing steps can be removed or modified while still remaining within the spirit and scope of the present teachings.

The exemplary method 200 can include supplying a precursor including an amount of each of aminopropyltriethoxysilane, $AgNO_3$, DI water, and ethanol at 210. At 220, the supplied precursor of an amount of each of aminopropyltriethoxysilane, $AgNO_3$, DI water, and ethanol can be atomized into droplets suspended in a carrier gas. The atomized mixture can be heated at 230 at a predetermined temperature for a predetermined time sufficient to reduce the Ag by ethanol to its elemental form of nano structured particles within a silica matrix shell. The predetermined time and temperature can include time and temperature in one or more of the drying zone and the heating zone of the furnace. A dilution gas can be supplied at 240 to the nano silver core shell structure in order to disperse and collect the particles. The resulting nano-structured particles can be collected at 250. Collection can include trapping the nano-structured particles on a filter paper at 260. The method can conclude with exhaustion of remaining gas at 270. Exhaustion of the gas can be by vacuum pump or the like. The method achieves a one-step synthesis of nano-structured particles. Further, the nano-structured particles can be well dispersed nano silver in a silica matrix.

Chosen features of the Ag-silica nano-composite can be controlled during the method 200 by selectively adjusting any of the precursor 122, including an aminosilane/Ag ratio in the precursor, evaporation rate of the atomized mixture in the furnace 140, which can be dependent upon a heating temperature of the furnace, droplet density, and residence time within the drying 142 and heating 144 zones of furnace 140. Controllable features can include final particle size, morphology, silver crystallite/cluster size, and silver distribution within the silica matrix.

An example for generating a nano silver-silica composite anti-microbial agent is provided in the following. One of ordinary skill in the art will understand that the example provided is exemplary and that other steps can be added or existing steps can be removed or modified while still remaining within the spirit and scope of the present teachings.

Example 1

A homogeneous solution of 5 g aminopropyltriethoxysilane (AMPTES), 0.5-2 g $AgNO_3$, 25 g DI water, and 12 g ethanol were sprayed/atomized into a glass aerosol reactor. The reactor was maintained at a temperature of about 400° C. within a Lindberg furnace. Spraying was with a TSI 9302A atomizer using nitrogen as a carrier gas. Pressure drop at a pinhole of the atomizer was set as 20 psi. The residence time was about 5 seconds. The powder was collected on PTFE filter paper.

The solvent, evaporation rate, aminosilane/Ag ratio in the precursor, heating temperature droplet density, and residence time all influence the final particle size, morphology, silver crystallite/cluster size, and silver distribution. X-ray diffraction (XRD), transmission electron microscopy (TEM), and energy dispersive spectroscopy (EDS) analysis can show that the silver nitrate can be easily reduced into elemental silver at the high temperature. In the final product, there are no evident XRD peaks for $AgNO_3$.

Figure 3D:
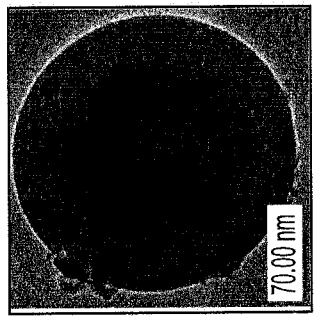
FIG. 3D depicts a nano Ag-silica particle.
Figure 3C:
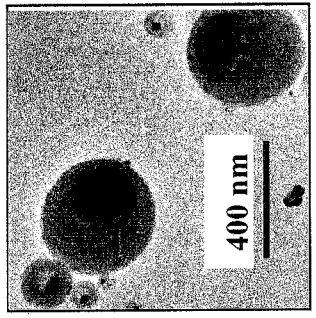
FIG. 3C depicts a multiple core Ag-silica particle.
Figure 3B:
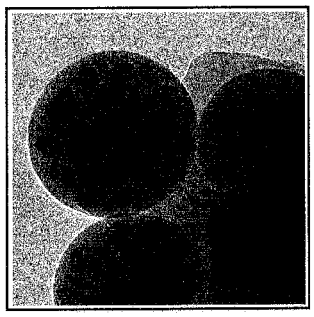
FIG. 3B depicts an eccentric single Ag core-$SiO_2$ particle.
Figure 3A:
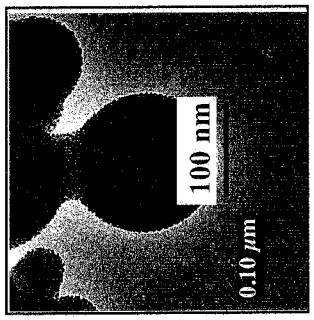
FIG. 3A depicts a centric single Ag core-$SiO_2$ particle.

Referring now to FIGS. 3A through 3D, various configurations of Ag-silica composite particles are depicted. FIG. 3A therefore depicts a centric single Ag core-$SiO_2$ particle, and FIG. 3B depicts acentric single Ag core-$SiO_2$ particles. The centric single Ag core-silica particles can be made by using tetraethoxysilane (TEOS) as the silica precursor. As illustrated in the figures, an increased hyrophobicity of the Ag-silica composite particles derived from using methyltriethoxysilane (MTES) instead of TEOS results in a shift of the Ag core from the center (FIG. 3A) to the edge (FIG. 3B) of the body.

In a hydrophilic silica matrix, decreasing the $AgNO_3$ solubility in the precursor and the diffusivity in the silica matrix favors multiple smaller cores as illustrated in each of FIGS. 3A, 3C and 3D. As shown in FIG. 3D, nano Ag crystallites/clusters can be uniformly dispersed in the silica matrix. X-ray photoelectron spectroscopy analysis shows that at particle surface the Ag/Si atomic ratio is 0.108, and 84.4% of silver is metallic, while 15.6% of silver exists as $Ag_2O$ after oxidation by surface oxygen. The particle sample in FIG. 3D is particularly effective for inhibiting bioactivity because the pathogen can directly contact silver nanoparticles on the surface of the particle. Further, the silver nanoparticles can be contacted or released continuously by diffusion after silica is worn out or dissolved gradually, thereby providing a lengthy disinfection time and high efficiency for a given Ag loading.

Figure 4:
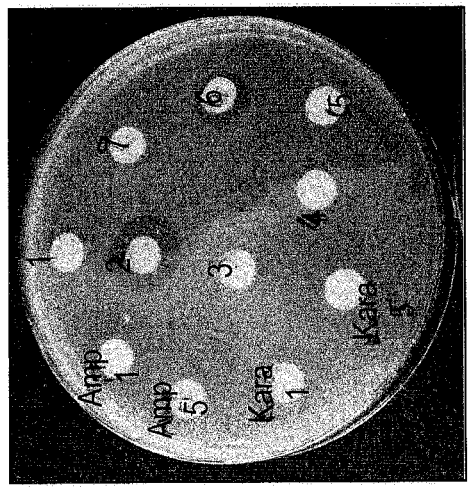
FIG. 4 illustrates an inhibition effect of various samples on E-coli.

Referring now to FIG. 4, formed nano-Ag particles were tested in a disc-diffusion assay following the Kirby-Bauer test (with some modification). The test showed a lack of *E coli* activity in the formed nano-Ag particles. In the test, filter paper discs (Whatman 3 mm, 7 mm in diameter) were sterilized by autoclave. All of the nanoparticles were dissolved or suspended in distilled water and impregnated in each disc (10 μg). The discs were air dried and stored at room temperature. Ampicillin (5 or 10 μg/disc) or kanamycin (5 or 10 g/disc) discs were used as controls. *E coli* strains DH5α (sensitive to ampicillin and kanamycin) and DH5α/Ampicillin$^r$ (sensitive to kanamycin) were cultured in LB broth (1% Trypton, 0.5% yeast extract, 1% NaCl, pH 7.0) overnight. The cultures were diluted for 10 fold in fresh LB broth and uniformly spread on the surface of LB agar plates (1.5% agar). With the disc dispenser, the full complement of the drug-impregnated cultures was applied to the discs. The plates were incubated for 24 hours at 37° C. Zones of inhibition were read with a metric ruler in millimeters as shown in Table 1 below. It was demonstrated that nanosilver-silica composite (FIG. 3, ~10 μg/disc) are superior to ampicillin in killing DH5α/Ampicillin-r strains, and comparable to kanamycin. There is no disinfection for the controls, fumed silica, titania nanoparticles, or porous silica particles with the single, big Ag core, indicating that direct contact of nanosilver with *E coli* is necessary for the disinfection. In the table, P25 is Degussa P25 titania nanoparticles made by the Degussa company. Another control, SiO$_2$/Ag (FIG. 3A) was made using tetraethoxysilate (TEOS) as silica precursor instead of aminopropyltriethoxysilane. SiO$_2$/Ag (FIG. 3D) is APTES derived well dispersed nano silver silica composite sample.

TABLE 1

(INHIBITION EFFECTS)

| | DH5α | DH5α/Ampicillin-r |
|---|---|---|
| Fumed SiO$_2$ | (—) | (—) |
| amino-functionalized SiO$_2$/Ag (FIG. 3D) | 15 mm | 16 mm |
| P25 | (—) | (—) |
| SiO$_2$/Ag (FIG. 3A) | (—) | (—) |
| Ampicillin 5 µg | 22 mm | (—) |
| Ampicillin 10 µg | 38 mm | (—) |
| Kanamycin 5 µg | 20 mm | 22 mm |
| Kanamycin 10 µg | 30 mm | 32 mm |

The aerosol method described herein can provide a continuous, low cost method for large scale production of advanced materials as the droplet and particles sizes, size monodispersity, evaporation rate, vapor liquid interfacial transport, and reactions can be well controlled. The process is fast, flexible, inexpensive, simple, easy to scale up, and causes less pollution than known methods. By controlling the sizes, silver distribution, and surface chemistry, the release can be controlled over a wide range. The silver nanoparticles with controllable size can be well dispersed and released in a controlled manner from a nontoxic silica matrix. The dry powders can be dispersed in water or can be lipophilic by chemical modification of the silica surface.

Silver nano composites are advantageous as they are extremely convenient for transportation, storage, and dispensation with required dosage, thermal stability and elongated disinfection time. By way of example, nano composites can be woven into fabrics or dispersed into electric appliances as pigments at high processing temperatures.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims.

As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of forming a nano structured composite particle comprising:
   spraying a mixture comprising aminosilane, AgNO$_3$, DI water, and alcohol in a carrier gas using an atomizer; and
   heating the mixture at a selected temperature for a time sufficient to reduce the AgNO$_3$ by the alcohol to form a plurality of nano structured composite particles comprising nano elemental silver and silica.

2. The method of claim 1, wherein a predetermined heating time is from about 0.01 to about 40 seconds.

3. The method of claim 1, wherein a selected heating temperature is from about 200 to about 800° C.

4. The method of claim 1, wherein the nano structured composite particles comprise silver in an amount of about 1 to about 80 wt % relative to the total weight of the composite particles.

5. The method of claim 1, wherein the mixture comprises a molar ratio of aminosilane to silver of about 0.1:1 to about 50:1.

6. The method of claim 1, wherein the aminosilane is present in an amount of about 5 g.

7. The method of claim 6, wherein the aminosilane is aminopropyltriethoxysilane.

8. The method of claim 1, wherein the mixture comprises about 0.5 g to about 2 g of $AgNO_3$.

9. The method of claim 1, wherein the mixture comprises about 25 g DI water.

10. The method of claim 1, wherein the mixture comprises about 12 g of ethanol.

11. The method of claim 1, wherein the carrier gas comprises one of nitrogen or air.

12. The method of claim 1, wherein each of the plurality of nano structured composite particles comprises a plurality of nano elemental silver particles at a contact surface of the each composite particle.

13. The method of claim 1, wherein each of the plurality of nano structured composite particles comprises a plurality of nano elemental silver particles dispersed throughout and at a contact surface of the each composite particle.

14. The method of claim 1, wherein each of the plurality of nano structured composite particles comprises a plurality of nano elemental silver particles dispersed throughout the each composite particle.

* * * * *